United States Patent
Zhao et al.

(10) Patent No.: US 11,690,717 B2
(45) Date of Patent: Jul. 4, 2023

(54) HEART VALVE CLAMP

(71) Applicant: LEPU MEDICAL TECHNOLOGY (BEIJING) CO., LTD., Beijing (CN)

(72) Inventors: Yang Zhao, Beijing (CN); Xiaojian Liu, Beijing (CN); Yuxin Zhang, Beijing (CN); Zhongjie Pu, Beijing (CN)

(73) Assignee: LEPU MEDICAL TECHNOLOGY (BEIJING) CO., LTD., Beijing (CN)

( * ) Notice: Subject to any disclaimer, the term of this patent is extended or adjusted under 35 U.S.C. 154(b) by 98 days.

(21) Appl. No.: 17/056,580

(22) PCT Filed: Mar. 30, 2020

(86) PCT No.: PCT/CN2020/081982
§ 371 (c)(1),
(2) Date: Nov. 18, 2020

(87) PCT Pub. No.: WO2021/195823
PCT Pub. Date: Oct. 7, 2021

(65) Prior Publication Data
US 2021/0298900 A1    Sep. 30, 2021

(51) Int. Cl.
*A61F 2/24* (2006.01)
*A61B 17/122* (2006.01)
*A61B 17/128* (2006.01)

(52) U.S. Cl.
CPC ........ *A61F 2/2436* (2013.01); *A61B 17/1222* (2013.01); *A61B 17/1285* (2013.01);
(Continued)

(58) Field of Classification Search
CPC .............. A61F 2/2436; A61F 2250/001; A61F 2220/0075; A61F 2220/0016;
(Continued)

(56) References Cited

U.S. PATENT DOCUMENTS

| 10,245,144 B1 | 4/2019 | Metchik et al. |
| 2015/0257883 A1* | 9/2015 | Basude ................. A61F 2/2466 623/2.11 |

(Continued)

FOREIGN PATENT DOCUMENTS

| CN | 106178986 A1 | 12/2016 |
| CN | 107666868 A | 2/2018 |

(Continued)

OTHER PUBLICATIONS

European Patent Office "Search Report", in Application No. 20803730.9-1113, dated Jul. 1, 2021, 8 pages.
Claims in Application No. 20803730.9-1113, dated Jul. 1, 2021, 4 pages.

*Primary Examiner* — Bruce E Snow
(74) *Attorney, Agent, or Firm* — Hickman Becker Bingham Ledesma LLP (57) ABSTRACT

The application relates to a heart valve clamp, comprises a fixed arm mechanism, a clamping arm mechanism, and a driving mechanism. The fixed arm mechanism comprises a fixed arm body and at least two fixed arms, extending outward from the fixed arm body, and integrally formed with the fixed arm body. The clamping arm mechanism comprises a clamping arm body connected to a bottom of the fixed arm body, and at least two clamping arms extending outward from the clamping arm bodies and integrally formed with the clamping arm body; and the driving mechanism comprises a second driving assembly that drives the fixed arm and the clamping arm to open or close. The fixed arm mechanism and the clamping arm mechanism of the entire heart valve clamp respectively forms an integral form, which can avoid the risk of the fixed arm or the clamping arm being disengaged, the stability of the whole structure is better. The fixed arm and the clamping arm clamp the valve leaflets under three-dimensional ultrasound and angiography navigation, so that the regurgitation area is reduced, which is (Continued)

capable of treating mitral or tricuspid regurgitation while keeping heat beating.

15 Claims, 11 Drawing Sheets

(52) U.S. Cl.
CPC ............... *A61F 2210/0014* (2013.01); *A61F 2220/0016* (2013.01); *A61F 2220/0075* (2013.01); *A61F 2250/001* (2013.01)

(58) Field of Classification Search
CPC ............ A61F 2210/0014; A61F 2/24; A61B 17/1285; A61B 17/1222
See application file for complete search history.

(56) References Cited

U.S. PATENT DOCUMENTS

| | | | |
|---|---|---|---|
| 2018/0296331 A1* | 10/2018 | Dixon | A61F 2/2403 |
| 2019/0000623 A1 | 1/2019 | Pan et al. | |
| 2019/0350710 A1* | 11/2019 | Ketai | A61B 17/0401 |
| 2020/0315786 A1 | 10/2020 | Metchik et al. | |

FOREIGN PATENT DOCUMENTS

| | | |
|---|---|---|
| CN | 109963529 A | 7/2019 |
| CN | 107789017 A | 3/2020 |
| CN | 211381986 U | 9/2020 |
| CN | 211381987 U | 9/2020 |
| WO | WO 2006/086434 | 8/2006 |
| WO | WO2018/209313 A1 | 11/2018 |

* cited by examiner

HEART VALVE CLAMP

RELATED APPLICATION

This application claims priority under 35 U.S.C. 119 to PCT/CN2020/081982, entitled "HEART VALVE CLAMP" and filed on Mar. 30, 2020, the contents of which are herein incorporated in their entirety by reference for all purposes.

TECHNICAL FIELD

The application relates to the technical field of medical equipment, in particular to a heart valve clamp.

BACKGROUND

The mitral valve is a one-way valve located between a left atrium and left ventricle of the heart. A normal and healthy mitral valve can control the blood to flow from the left atrium to the left ventricle, while avoiding the blood flowing from the left ventricle to the left atrium. With the development of society and the aging of the population, the incidence rate of mitral regurgitation (MR) is on the rise, and the mitral regurgitation has become a common heart valve disease.

At present, the treatment of mitral regurgitation has experienced the era of a traditional surgical median sternal incision surgery and recently a minimally invasive small incision surgery, and currently an era of transcatheter intervention treatment is coming. Interventional minimally invasive treatment of mitral regurgitation has become one of the most popular research directions in interventional cardiology. The interventional MR method with less trauma, less complications and less cost, has made great progress.

In the field of mitral valve regurgitation, mitral valve regurgitation interventional treatment techniques can be comprises two types: one is transcatheter mitral valve repair, such as MitraClip, PASCAL, ValveClamp, Cardioband, Mitralign and NeoChord, etc., the other type is a transcatheter mitral valve implantation. Currently a repairing surgery is the main treatment. However, there are still some problems in the current technology. For example, in MitralClip, the anterior and posterior leaflets of the mitral valve are clamped, which turns a large single hole into two small holes to achieve a treatment purpose, but the path for implantation is too long and the operation is too complicated, therefore, the repairing surgery needs to be improved.

In the prior art, there is a valve clamp and a valve clamping system, the valve clamping system comprises a valve clamp and a pushing device. The valve clamp comprises a push rod, at least two clamp, at least one extension arm, and a driving assembly for driving the clamp to open and close and the extension arm to stretch and retract. Each clamp comprises a first clamp arm and a second clamp arm that can be opened and closed relatively, and at least one extension arm is telescopically arranged on the surface of the first clamp arm. During surgery, the first clamp arm and the second clamp arm can be opened and closed, so that the valve leaflets located between the first clamp arm and the second clamp arm can be clamped.

However, the above valve clamp comprises two or more of first clamp arms and two or more of the second clamp arms, and each of the first clamp arms or the second clamp arms is separately arranged. In other words, during production and processing, each clamp arm is assembled with the push rod or driving assembly in a middle part for assembly, which is weak in integrity, and there may be a risk of a partial disconnection as the connection is not stable enough.

SUMMARY

The purpose of the present application is to provide a heart valve clamp to solve the technical problem that the clamp arms in the prior art are separately arranged, which results in that the connection is not stable enough and there may be a risk of disconnection.

In order to achieve the above objective, the technical solution of the present application is to provide a heart valve clamp, comprising, a fixed arm mechanism comprising a fixed arm main body and at least two fixed arms, extending outward from the fixed arm main body, and integrally formed with the fixed arm main body; a clamping arm mechanism comprising a clamping arm main body connected to a bottom of the fixed arm main body and at least two clamping arms extending outward from the clamping arm main bodies and integrally formed with the clamping arm main body; and a driving mechanism comprising a first driving assembly that drives the fixed arm to open or close in relative to the fixed arm main body, and a second driving assembly that drives the clamping arm to open or close in relative to the clamping arm main body.

Further, the fixed arm body has a tube structure, and a side wall of the tube structure is provided with a first strip groove, and a pipe wall disposed in the first strip groove is the fixed arm.

Further, the heart valve clamp further comprises a delivery sheath fixed on a top of the fixed arm body.

Further, the fixed arm mechanism further comprises a sheath hanger on the top of the fixed arm body.

Further, the sheath hanger is detachably and fixedly connected with the delivery sheath.

Further, the sheath hanger has at least one T-shaped hook protruding from the top of the fixed arm body and a fixing groove is arranged at a bottom of the delivery sheath for receiving the sheath hanger, and the fixing groove is engaged with the sheath hanger and can be bent and separated from the engagement.

Further, the fixed arm is preformed to open in a direction away from the fixed arm main body, and the first driving assembly comprises at least two pulling wires, and an end of each pulling wire is respectively fixedly connected to a fixed arm and drives a single fixed arm or a plurality of fixed arms to open or close.

Further, a fixing hole is arranged at an end of the fixed arm away from the fixed arm body for fixing the pulling wire.

Further, a barbed structure is arranged on one side of the fixed arm facing the clamping arm.

Further, the clamping arm mechanism further comprises a pulling arm base and at least two pulling arms extending outward from the pulling arm base, and the pulling arm base is located at a bottom of the clamping arm main body, and the pulling arm is fixedly connected to or integrally formed with the clamping arm, and a connection point between the pulling arm and the clamping arm is spaced apart from the clamping arm main body.

Further, the pulling arm base is a tube structure, and a side wall of the tube structure is provided with a second strip groove, a tube wall disposed in the second strip groove is regarded as the pulling arm, and a tube wall disposed outside the second strip groove is provided with a third strip groove, and an inner tube wall of the third strip groove forms the clamping arm and the clamping arm main body.

Further, the second driving assembly comprises a push rod slidably disposed through the fixed arm body and the clamping arm main body and abutting against the pulling arm base.

Further, the clamping arm is preformed to fit on the clamping arm main body, and the push rod can drive the pulling arm base to move toward a side away from the clamping arm main body, and drive the clamping arm to open.

Further, there are two fixed arms and two clamping arms, the two fixed arms are symmetrical, the two clamping arms are symmetrical, and the fixed arms are arranged directly opposite to the clamping arms.

Further, a maximum opening angle of the fixed arm is greater than or equal to a maximum opening angle of the clamping arm.

Further, the fixed arm mechanism and the clamping arm mechanism are both made of shape memory alloy.

Further, an external edge of each of the fixed arm and the clamping arm is configured to have a fillet or chamfer.

Further, an external side of each of the fixed arm mechanism and the clamping arm mechanism is covered with fiber suture cloth.

The beneficial effects of the heart valve clamp of the present application are as follows: compared with the prior art, the fixed arm mechanism and the clamping arm mechanism of the entire heart valve clamp respectively forms an integral form, and there is a fixed connection between the fixed arm mechanism and the clamping arm mechanism, which can avoid the risk of the fixed arm or the clamping arm being disengaged, the stability of the whole structure is better, the open or close is driven by the first driving assembly and the second driving assembly separately, the fixed arm and the clamping arm clamp the valve leaflets under three-dimensional ultrasound and angiography navigation, so that the regurgitation area is reduced, and the transcatheter edge-to-edge repair can be achieved, which is capable of treating mitral or tricuspid regurgitation with keeping heat beating, and has a simpler structure and more convenient manufacturing.

BRIEF DESCRIPTION OF THE DRAWINGS

In order to describe the specific embodiments of the present application or the technical solutions in the prior art more clearly, the drawings used in the specific embodiments or the description of the prior art will be introduced briefly. Obviously, the drawings represent some embodiments of the present application and other drawings can be obtained based on these drawings without paying inventive work for a person skilled in the art.

REFERENCE SIGNS

100. fixed arm mechanism; 200. clamping arm mechanism; 300. push rod; 400. delivery sheath; 500. pulling wire; 600. leaflet; 110. fixed arm body; 120. fixed arm; 130. first strip groove; 140. sheath hanger; 121. fixing hole; 122. barbed structure; 210. clamping arm body; 220. clamping arm; 230. pulling arm base; 240. pulling arm; 250. second strip groove; 260. third strip groove; 410. fixing groove.

DETAILED DESCRIPTION

The present application will be further described in detail below with reference to the drawings and examples. Obviously, the described embodiments represent part of, but not all of the embodiments of the present application. Based on the embodiments of the present application, all other embodiments obtained by a person skilled in the art without inventive work shall fall within the scope of the present application.

In the description of the present application, it should be understood that the terms "center", "upper", "lower", "left", "right", "vertical", "horizontal", "inside" and "outside" indicate orientation or positional relationship which are based on the orientation or positional relationship shown in the drawings, and it is merely for convenience of describing the present application and simplifying the description, rather than indicating or implying that the indicated device or element must have a particular orientation, and be constructed and operated in a particular orientation. Therefore these terms should not be understood as limiting the scope of the present application. In addition, the terms "first", "second", and "third" are only used for descriptive purposes, and cannot be understood as indicating or implying relative importance.

In the description of the present application, unless otherwise explicitly stated or specified, it should be noted that the terms "mounted", "connected" and "connecting" should be understood in a broad sense. For example, a connection can be a fixed or detachable connection, or an integral connection; a mechanical connection or an electrical connection; a direct or indirect connection through an intermediate medium, and it can be an internal communication between two elements. For a person skilled in the art, the specific meaning of the above-mentioned term in the present application can be understood in specific situation.

In the present application, "proximal end" and "distal end" refers to a relative orientation, relative position and relative direction of the elements or actions among each other from the perspective of the surgeon using a medical device, although "proximal end" and "distal end" are not restrictive, and the "proximal end" usually refers to an end of the medical device that is close to the surgeon during normal operation, and the "distal end" usually refers to the end that firstly enters the human body of the patient.

In addition, the technical features involved in the different embodiments of the present application described below can be combined with each other as long as they do not conflict with each other.

Figure 1:
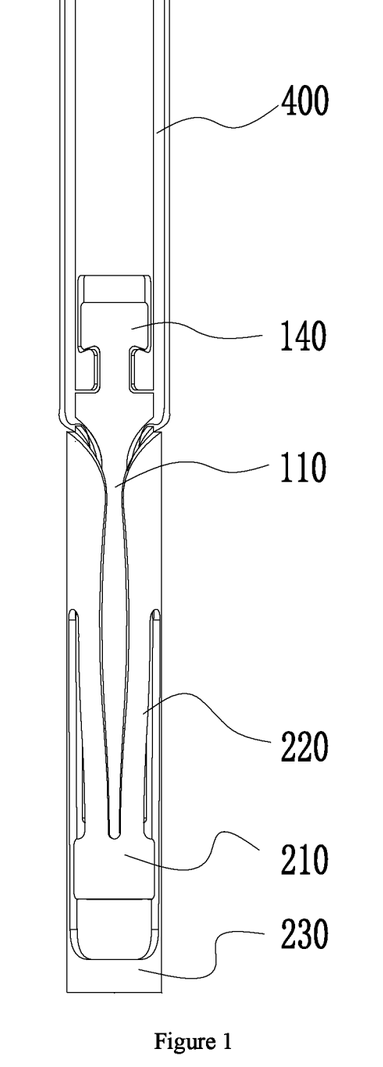
FIG. 1 illustrates a schematic structural view of the heart valve clamp in a closed state of an embodiment of the present application when it is folded.
Figure 2:
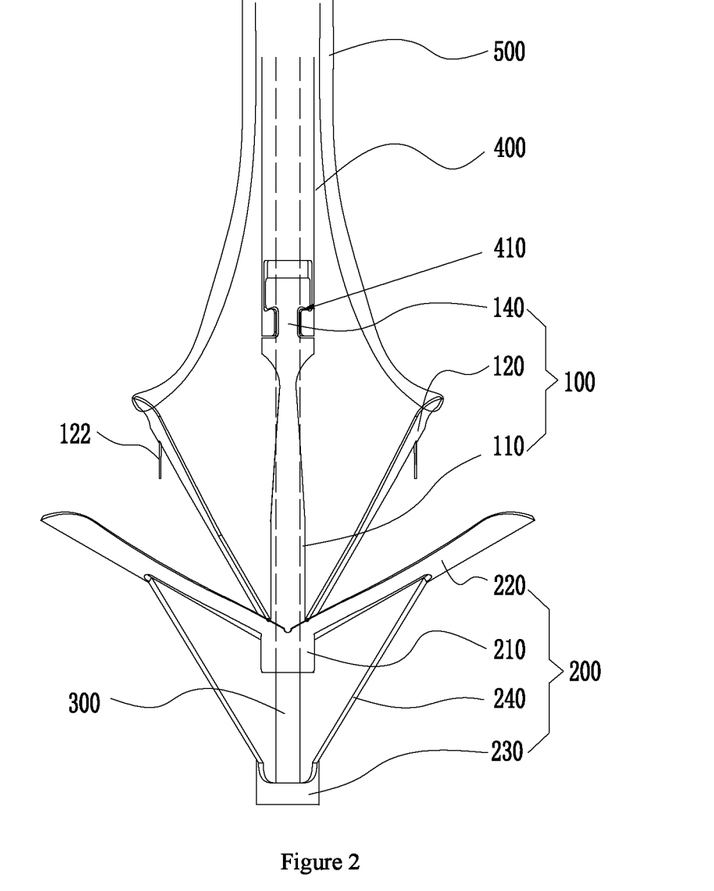
FIG. 2 illustrates a schematic structural view of the heart valve clamp in an opened state of an embodiment of the present application.

As shown in FIG. 1 and FIG. 2, the heart valve clamp comprises a delivery sheath 400, a fixed arm mechanism 100 fixed to a bottom of the delivery sheath 400, a clamping arm mechanism 200 sleeved on a bottom of the fixed arm body 110, and a driving mechanism to drive the clamping arm 220 and the fixed arm 120 to open and close. The fixed arm mechanism 100 comprises a fixed arm body 110 fixedly connected to the bottom of the delivery sheath 400 and at least two fixed arm bodies 120 extending outward from the fixed arm body 110, fixed ends of the fixed arm 120 are integrally formed with the fixed arm body 110; the clamping arm mechanism 200 comprises a clamping arm body 210 sleeved on the bottom of the fixed arm body 110 and at least two clamping arms 220 extending outward from the clamping arm body 210, fixed ends of the clamping arms 220 are integrally formed with the clamping arm body 210. The driving mechanism comprises a first driving assembly to drive the fixed arm 120 to open or close toward the clamping arm 220 and a second driving assembly to drive the clamping arm 220 to open or close toward the fixed arm 120.

Compared with the prior art, the heart valve clamp of the present application can enter the left atrium under the drive of the delivery sheath 400. Each of the fixed arm mechanism 100 and the clamping arm mechanism 200 is respectively regarded as an integral component, and the fixed arm mechanism 100 and the clamping arm mechanism 200 are fixedly connected, which can avoid the risk of a disconnection of the fixed arm 120 or the clamping arm 220, and results in a more stable overall structure. In addition, the first driving assembly and the second driving assembly separately drive opening or closing action, and the fixed arm 120 and the clamping arm 220 are used to clamp the valve leaflet 600 under three-dimensional ultrasound and angiography navigation, thereby reducing a regurgitation area and realizing a transcatheter edge-to-edge repair. The treatment of mitral valve regurgitation or tricuspid regurgitation can be performed with keeping heart beating, and the structure of the heart valve clamp is simpler, and the manufacturing thereof is more convenient.

Figure 3:
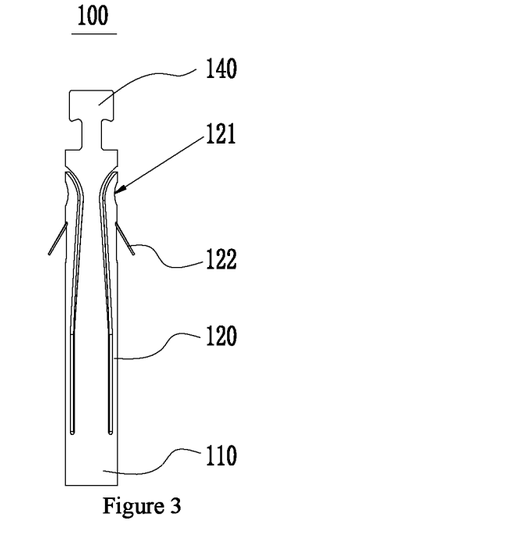
FIG. 3 illustrates a schematic structural side view of a fixed arm mechanism in a closed state of an embodiment of the present application.
Figure 4:
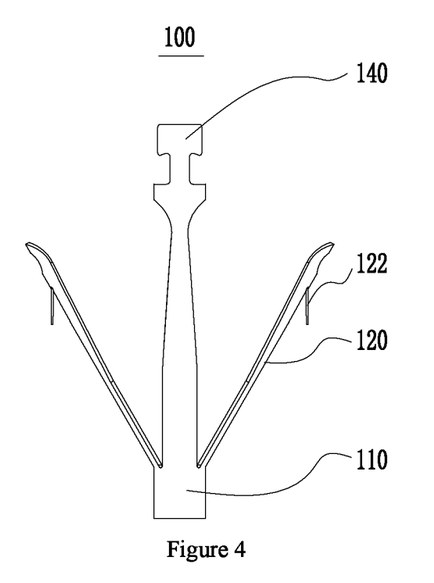
FIG. 4 illustrates a schematic structural view of a fixed arm mechanism in an opened state of an embodiment of the present application.
Figure 5:
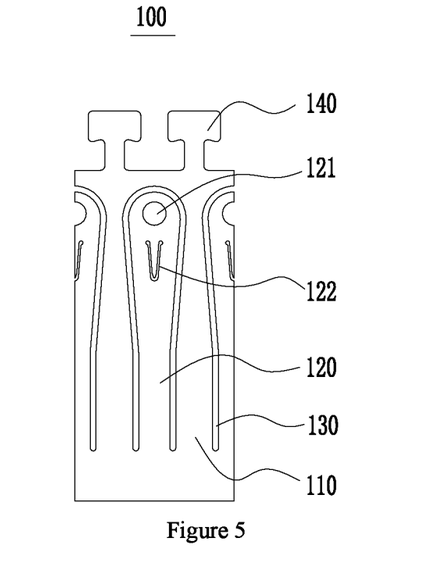
FIG. 5 illustrates a schematic structural view of a fixed arm mechanism in an opened state of an embodiment of the present application.
Figure 6:
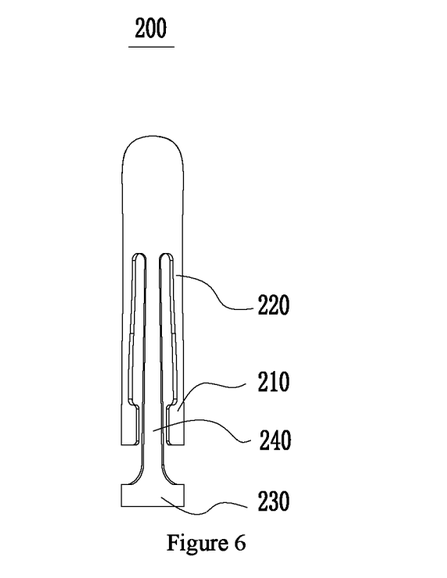
FIG. 6 illustrates a schematic side view of the structure of a clamping arm mechanism in an closed state of an embodiment of the present application.
Figure 7:
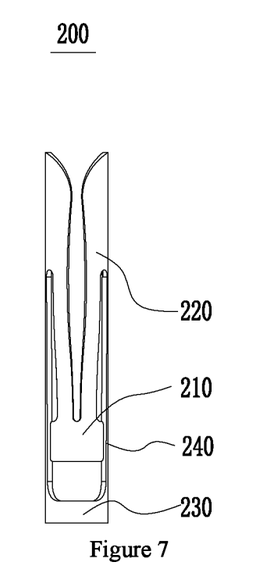
FIG. 7 illustrates another schematic structural side view of a clamping arm mechanism in a closed state of an embodiment of the present application.
Figure 8:
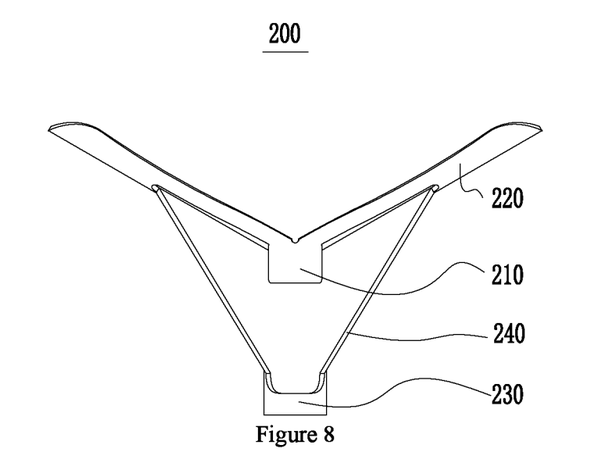
FIG. 8 illustrates a schematic structural view of a clamping arm mechanism in an opened state of an embodiment of the present application.

Further, as shown in FIGS. 3 to 5, as a specific embodiment of the heart valve clamp of the present application, the fixed arm body 110 has a tube structure, and a first strip groove 130 is arranged on a side wall of the tube structure, and the tube wall disposed in the first strip groove 130 is the fixed arm 120. Specifically, the first strip groove 130 is a groove disposed on the tube structure which has an elongated shape and can be enclosed to fit the shape of the fixed arm 120, so that a top of the fixed arm 120 can be separated from the body of the fixed arm 110, and a bottom of the fixed arm 120 is still connected to the fixed arm body 110. That is, the fixed arm 120 has a fixed end in a fixed connection with the fixed arm body 110 and a free end that can rotate around the fixed arm body 110 to open. The entire fixed arm mechanism 100 is integrally formed from a tube structure, which has better integrity and is convenient for manufacturing, processing and assembly, thereby greatly saving the assembly process. Certainly, according to actual conditions and specific needs, in other embodiments of the present application, only the fixed arm body 110 can be a tube structure, and the fixed arm 120 is an extension part disposed at the top of the tube structure, which is not exclusively limited herein.

Further, referring to FIGS. 1 to 5, as a specific embodiment of the heart valve clamp of the present application, the fixed arm mechanism 100 further comprises a sheath hanger 140 on a top of the fixed arm body 110, the sheath hanger 140 is detachably and fixedly connected to the delivery sheath 400. Specifically, the sheath hanger 140 is used to connect the delivery sheath 400, and the delivery sheath 400 is one of introducing catheters, which can be inserted into the left ventricle, and the sheath hanger 140 is arranged at a top of the fixed arm mechanism 100 so as to realize a detachable connection between the entire fixed arm mechanism 100 and the delivery sheath 400 through the sheath hanger 140, thereby realizing a fixed connection between the clamping arm mechanism 200 and the delivery sheath 400 and ensuring that the fixed arm mechanism 100 and the clamping arm mechanism 200 can move together with the delivery sheath 400, and after the fixed arm 120 and the clamping arm 220 respectively clamp the leaflet 600, the fixed arm mechanism 100 and the delivery sheath 400 can be removed, and only the fixed arm mechanism 100 and the clamping arm mechanism 200 remain in the ventricle.

Further, referring to FIGS. 1 to 5, as a specific embodiment of the heart valve clamp of the present application, the sheath hanger 140 comprises at least a T-Shape hook structure protruding from a top of the fixed arm body 110, and a bottom of the delivery sheath 400 is provided with a fixing groove 410 for receiving the sheath hanger 140. Specifically, the sheath hanger 140 has a T-shape hook structure, and the fixing groove 410 is a T-shape groove. The T-shape hook structure can be arranged in the T-shape groove to realize a connection between the sheath hanger 140 and the delivery sheath 400, and at this time the push rod 300 can be inserted into the interior of the delivery sheath 400 and the sheath hanger 140. The push rod 300 can limit a relative bending between the delivery sheath 400 and the sheath hanger 140, that is the sheath hanger 140 is always engaged inside the fixing groove 410. When the operation is completed, the push rod 300 can be withdrawn from the delivery sheath 400. At this time, the delivery sheath 400 and the sheath hanger 140 can be bent relatively, and the delivery sheath 400 is moved to bend sheath hanger 140, then the sheath tube hanger 140 can be pulled out of the fixing groove 410, so as to realize a separation between the delivery sheath 400 and the sheath hanger 140. The above method for separation is simple and can cooperate with the push rod 300 to achieve separation, thereby effectively avoiding misoperation, and realizing the separation between the delivery sheath 400 and the sheath hanger 140. In addition, the operation is convenient, and the time for operation is shortened, and the operation difficulty and risk are reduced.

Certainly, according to actual conditions and specific needs, in other embodiments of the present application, threads may be formed on both external surface of the sheath hanger 140 and the inner surface of the delivery sheath 400, and then a detachable connection between the sheath 400 and the sheath hanger 140 can be realized by a threaded connection, which is not exclusively limited herein.

Preferably, an external diameter of the push rod 300 matches an inner wall of the delivery sheath 400 and the fixed arm body 110, so that the push rod 300 can slide in the delivery sheath 400 and the fixed arm body 110, and can be completely filled in the delivery sheath 400 and the fixed arm body 110, that is, the external diameter of the push rod 300 is less than or equal to an inner diameter of the delivery sheath 400, and the external diameter of the push rod 300 is less than or equal to the inner diameter of the fixed arm body 110.

Further, as shown in FIGS. 1 to 5, as a specific embodiment of the heart valve clamp of the present application, the fixed arm 120 is preformed to be opened toward a side away from the fixed arm body 110, and the first driving assembly comprises at least two pulling wires 500, and ends of the pulling wires 500 are fixedly connected to free ends of the fixed arms 120. Specifically, in an use state, the fixed arm 120 is to be opened toward the side away from the fixed arm body 110, and in a delivery state, the fixed arm 120 is to be closed on both sides of the fixed arm body 110, and the fixed arm 120 is to be performed to a certain angle which is to be greater than a maximum opening angle of the clamping arm 220, so that the fixed arm 120 can cooperate with the clamping arm 220 to clamp the leaflet 600 when fixed arm 120 is naturally opened, and it can be ensured that the clamping arm 220 can clamp and fix the valve leaflet 600 when clamping arm 220 is opened to a maximum angle. In the delivery sheath, a left arm 120 and right fixed arm 120 are kept closed under a tightening action of pulling wires 500. After reaching a designated position, the fixed arm 120 is released by relaxing the pulling wire 500 to be opened to a certain angle to realize an open of the fixed arm 120. The fixed arm 120 has a preformed opening angle of about 1200 to 240°, and the rod width, structure, and tube wall thickness of the fixed arm 120 determine that a force of the fixed valve leaflet 600 after the fixed arm 120 is opened can be adjusted according to different types of lesions.

The pulling wire 500 is used to realize a drive structure for opening or closing the fixed arms 120, so that each fixed arm 120 can be separately opened, which can realize an unilateral adjustment and fully retractable function, and meet a variety of different surgical needs, in addition, the above structure is simple and convenient for operation.

Further, as shown in FIG. 5, as a specific embodiment of the heart valve clamp of the present application, the fixed arm 120 is provided with a fixing hole 121 at an end away from the fixed arm body 110 for fixing the pulling wire 500. Specifically, the fixing hole 121 is arranged at a free end of the fixed arm 120, and one end or a middle part of the pulling wire 500 can pass through the fixing hole 121, so as to connect the fixing hole 121. The end of the pulling wire 500 can be directly tied to or fixed in the fixing hole 121. At this time, the other end of the pulling wire 500 extends through an inner part of the delivery sheath 400 to the outside of human body, and the surgeon can pull the other end of the pulling wire 500 to control the fixed arm 120. After the operation is completed, the pulling wire 500 can be cut off by scissors, or a dissolvable pulling wire 500 can be used. Optionally, a middle part of the pulling wire 500 can be used to pass through an inner part of the fixing hole 121, both ends of the pulling wire 500 extend through the inner part of the delivery sheath 400 to the outside of human body. The surgeon can simultaneously pull both ends of the pulling wire 500 to control the fixed arm 120. After the operation is completed, the surgeon pulls one end of the pulling wire 500, and the other end can be released from the fixing hole 121 after passing through the delivery sheath 400, so as to realize a removal of the pulling wire 500. The operation is relatively simple and the time for operation is shorter with lower risk.

Furthermore, as shown in FIGS. 3 to 5, as a specific embodiment of the heart valve clamp of the present application, the fixed arm 120 is provided with a barbed structure 122 on one side facing the clamping arm 220. Specifically, the barbed structure 122 comprises a plurality of protrusions arranged on a bottom surface of the fixed arm 120. When the fixed arm 120 is in a retracted state, a tip of the protrusion is inclined downward, that is, the tip is inclined toward the clamping arm 220; When the arm 120 is in an open state, the tip of the protrusion is also inclined downward, which can increase a friction to the fixed leaflet 600. The number of protrusions can be adjusted according to actual conditions, which can be one or more.

Further, as shown in FIGS. 2 and 6-9, as a specific implementation of the heart valve clamp of the present application, the clamping arm mechanism 200 further comprises a pulling arm base 230 and at least two pulling arms 240 extending outward from a pulling arm base 230, and the pulling arm base 230 is located at a bottom of the clamping arm body 210, and the pulling arm 240 and a bottom of the free end of the clamping arm 220 are fixedly connected or integrally formed. Specifically, the pulling arm base 230 is located at the bottom of the clamping arm body 210, and the pulling arm 240 is formed by extending the pulling arm base 230 upward, and the pulling arm 240 is connected to the pulling arm base 230, and the pulling arm 240 can also be opened or closed around the pulling arm base 230, so that the pulling arm 240 drives the opening and closing of the clamping arm 220. The opening and closing of the clamping arm 220 is controlled through the position of the pulling arm base 230. The pulling arm base 230, the pulling arm 240, the clamping arm 220, and the clamping arm body 210 can all be integrally formed; or the clamping arm 220 and the clamping arm body 210 can be integrally formed, and the pulling arm base 230 and pulling arm 240 are integrally formed, in addition, the clamping arm 220 and the pulling arm 240 are fixedly connected, which is not exclusively limited herein.

Figure 9:
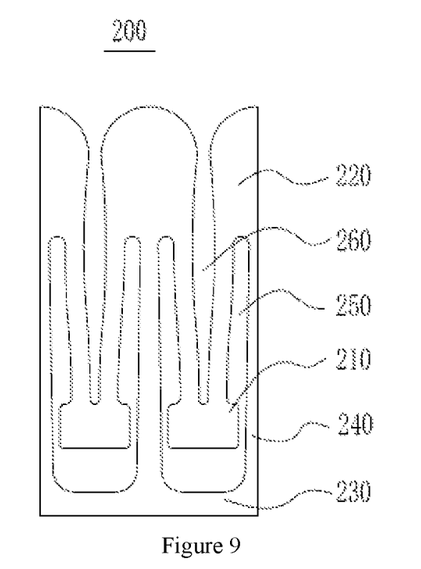
FIG. 9 illustrates a schematic structural view of a clamping arm mechanism in an opened state of an embodiment of the present application.
Figure 10:
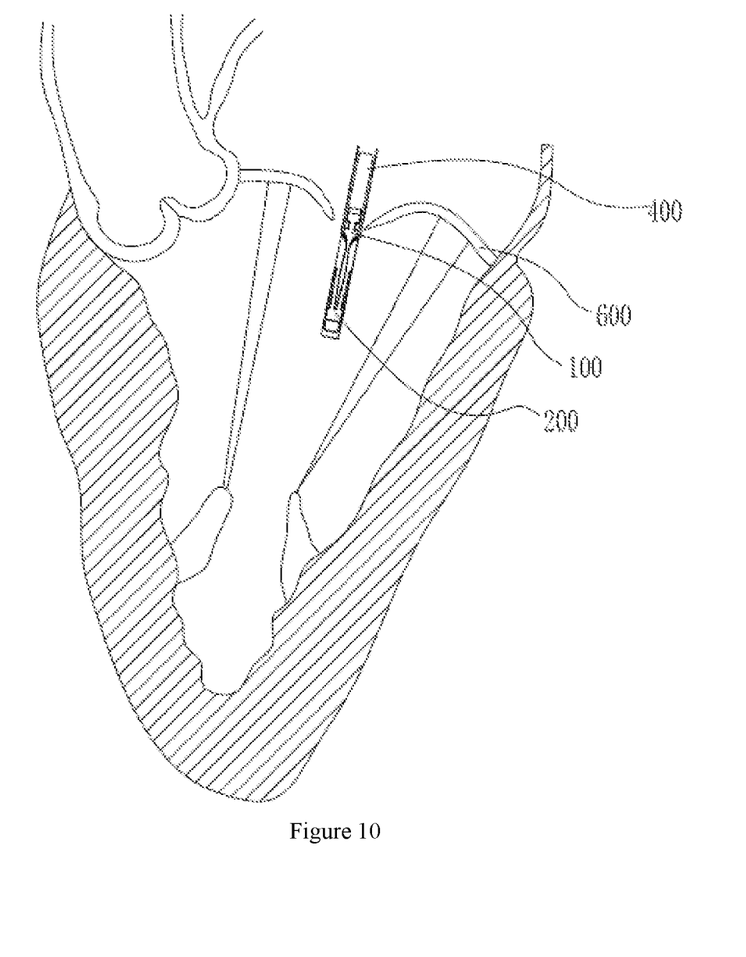
FIG. 10 illustrates a schematic structural view of a heart valve clamp inserted into the heart in an embodiment of the present application.
Figure 11:
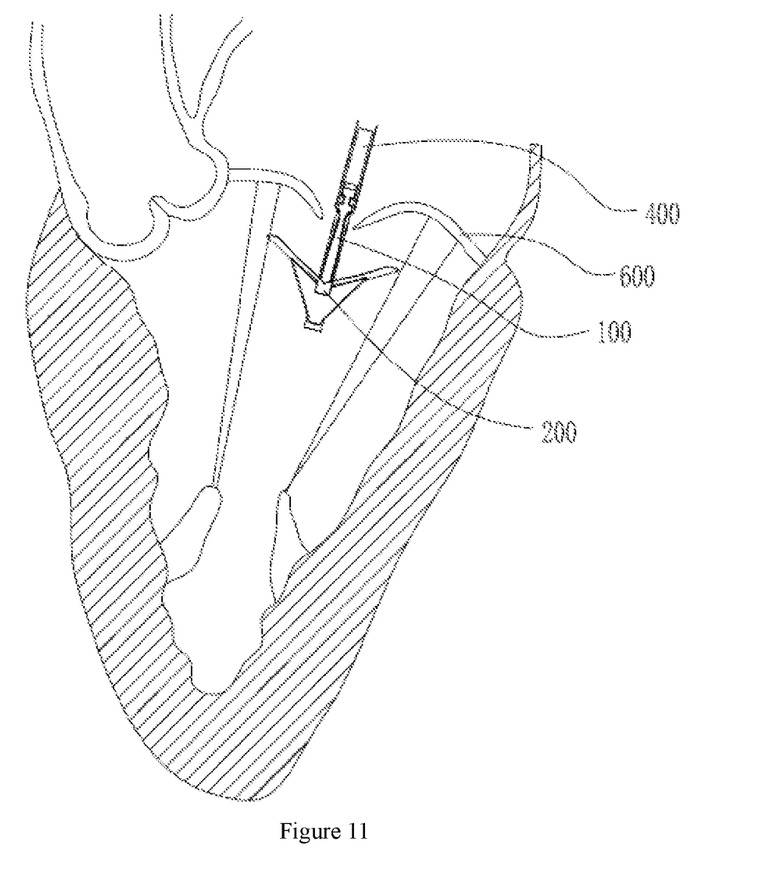
FIG. 11 illustrates a schematic structural view of a heart valve clamp with the clamping arms in an opened state of an embodiment of the present application.
Figure 12:
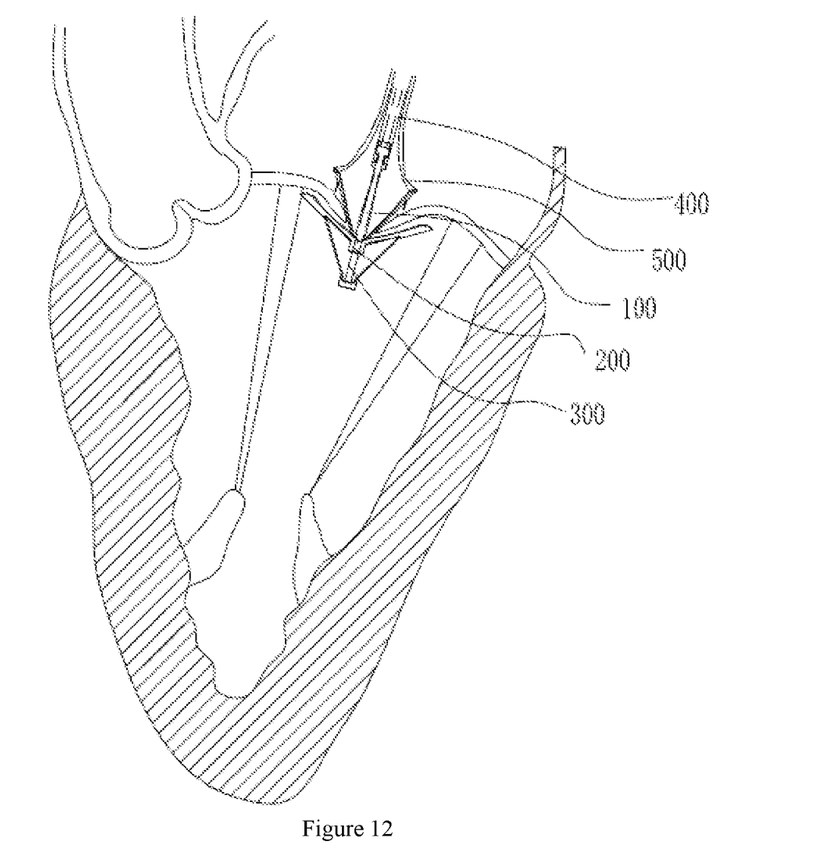
FIG. 12 illustrates a schematic structural view of a heart valve clamp with the fixed arms at both sides in an opened state of an embodiment of the present application.
Figure 13:
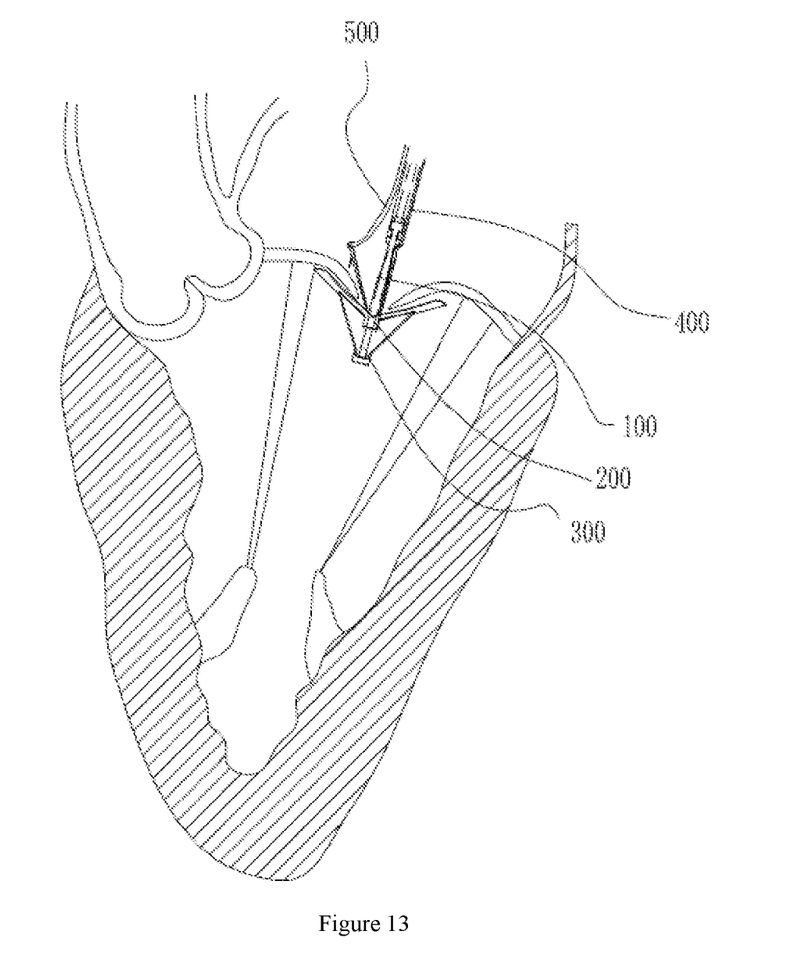
FIG. 13 illustrates a schematic structural view of a heart valve clamp with a fixed arm in an opened state of an embodiment of the present application.
Figure 14:
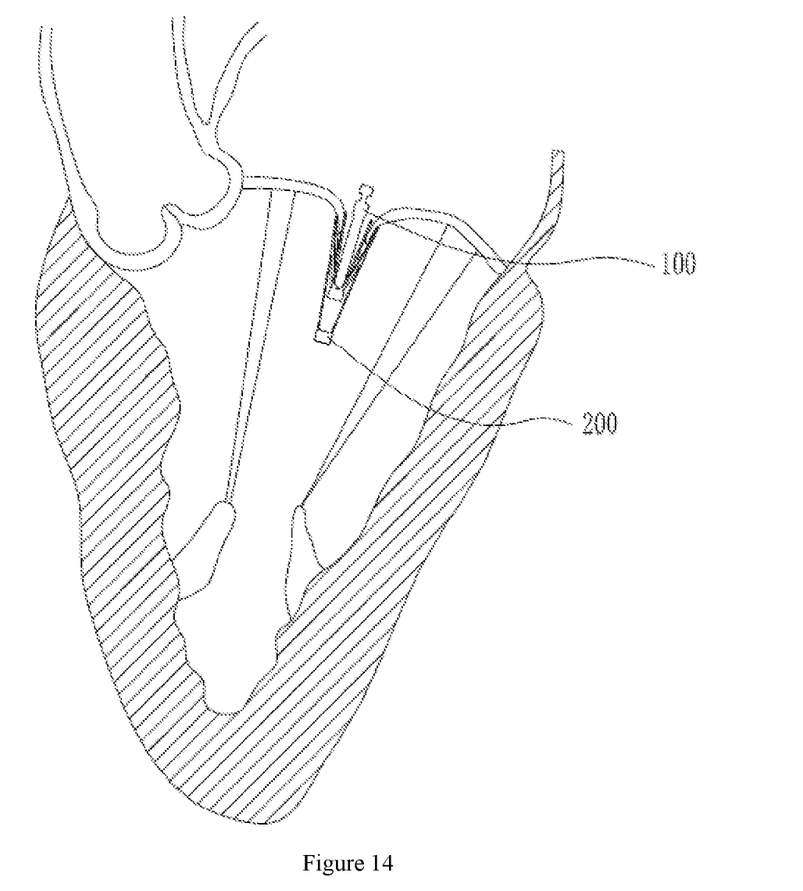
FIG. 14 illustrates a schematic structural view of the heart valve clamp of an embodiment of the present application when a fixation is completed.

Further, as shown in FIG. 9, as a specific embodiment of the heart valve clamp of the present application, the pulling arm base 230 has a tube structure, and a side wall of the tube structure is provided with a second strip grooves 250, and a tube wall arranged in the second strip groove 250 is the pulling arm 240, and a tube wall arranged outside the second strip groove 250 is provided with a third strip groove 260, and an inner tube wall of the third strip groove 260 forms the clamping arm 220 and the clamping arm body 210. Specifically, the second strip groove 250 is a groove disposed on the tube structure, which has an elongated shape and can be enclosed to match the shape of the pulling arm 240, so that a top of the pulling arm 240 and the pulling arm base 230 can be separated, and the bottom of the pulling arm 240 is still connected with the pulling arm base 230, that is, the pulling arm 240 also has a fixed end fixedly connected with the pulling arm base 230, and a free end to open rotatably around the pulling arm base 230. A third strip groove 260 is further arranged on the remaining tube wall, the third groove has an elongated shape and can be enclosed to have a shape as the clamping arm 220 and the body of the clamping portion, so that the top of the pulling arm 240 is connected with the top of the clamping arm 220, the bottom of the clamping arm 220 is fixedly connected to the clamping arm body 210, and an external edge of the clamping arm body 210 is separated from the pulling arm 240 and the pulling arm base 230. At this time, the entire clamping arm mechanism 200 is integrally formed by a tube structure, which has better integrity and is more convenient for manufacturing, processing and assembly, thereby greatly saving the assembly process. Certainly, according to actual conditions and specific needs, in other embodiments of the present application, the clamping arm body 210 may also have a tube structure, and the clamping arm 220 may be an extension part disposed at a top of the tube structure; the pulling arm base 230 has a tube structure, and the pulling arm 240 is an extension part disposed at a top of the tube structure, and the pulling arm 240 and the clamping arm 220 are fixedly connected, which is not exclusively limited herein.

Further, as shown in FIG. 2, as a specific embodiment of the heart valve clamp of the present application, the second driving assembly comprises a push rod 300 arranged in the delivery sheath 400, and the push rod 300 is arranged to slidably penetrates the fixed arm body 110 and the clamping arm body 210 and abuts against the pulling arm base 230. Specifically, the push rod 300 is arranged in the delivery sheath 400, and can be abutted against or detachably connected with the pulling arm base 230, and the push rod 300 drives the pulling arm base 230 to move, so that the push rod 300, the pulling arm 240 and the clamping arm 220 can form a link mechanism, and then the push rod 300 is moved to drive the pulling arm 240 and the clamping arm 220 to open or close. The push rod 300 can move in the fixed arm mechanism 100 and the clamping arm mechanism 200. When the push rod 300 moves to a distal end, the pulling arm base 230 is pulled to move, and then the pulling arm 240 is brought to open a certain angle γ, and finally the clamping arm 220 is opened to a corresponding angle β of about 0° to 210°. The angle β can be adjusted in real time by the relative position of the pulling arm 240, and the angle β is greater than the angle γ. A clamping force of the clamping arm 220 can be adjusted by the rod width of the clamping arm 220 and the pulling arm 240, a wall thickness and structure of the tube.

Further, as a specific embodiment of the heart valve clamp of the present application, the clamping arm 220 is preformed to fit on the clamping arm body 210, and the push rod 300 can drive the pulling arm base 230 to move toward a side away from the clamping arm body 210 and drives the clamping arm 220 to open. Specifically, in a use state, the clamping arm 220 needs to get close to a side near the clamping arm body 210, in a delivery state, the clamping arm 220 is closed naturally on both sides of the clamping arm body 210. When the valve leaflet 600 needs to be clamped, the clamping arm 220 is opened by the pulling arm 240, so that the clamping arm 220 is arranged on an inner side of the valve leaflet 600. After the fixed arm 120 is also fixed, the pushing rod 300 is removed and the pulling arm 240 doesn't exert a pulling force to stretch the clamping arm 220, but the clamping arm 220 has a relatively large return force to get close to the clamping arm body 210, and the fixed arm 120 also has a return force to get away from the fixed arm body 110, therefore, the clamping force between the clamping arm 220 and the fixed arm 120 can be well ensured to further ensure the clamping effect to the valve leaflet 600.

Further, as shown in FIGS. 2 and 6-9, as a specific embodiment of the heart valve clamp of the present application, the heart valve clamp comprises two fixed arms 120 and two clamping arms 220 respectively. The two fixed arms 120 are symmetrical, the two clamping arms 220 are symmetrical, and the fixed arms 120 and the clamping arms 220 are directly opposite. When there are two fixed arms 120 and two clamping arms 220, the fixed arm 120 and the clamping arm 220 can be symmetrically arranged to be applied in the treatment of mitral valve regurgitation, which can ensure uniformity of the force applied to the valve leaflet 600 by the entire heart valve clamp, and that the fixed arm 120 and the clamping arm 220 are directly aligned to ensure accurate clamping of the valve leaflet 600. Certainly, according to actual conditions and specific needs, in other embodiments of the present application, the fixed arm 120 and the clamping arm 220 can also be arranged asymmetrically, and there may be three or more of the fixed arm 120 and the clamping arm 220, which can be used in the treatment of tricuspid regurgitation or multiple tricuspid regurgitation, which is not exclusively limited herein.

Further, as a specific embodiment of the heart valve clamp of the present application, the fixed arm mechanism 100 and the clamping arm mechanism 200 are both made of shape memory alloy. Specifically, the shape memory alloy refers to a metal that can retain the memory of an initial shape, that is, the fixed arm 120 is preformed to open toward a side away from the fixed arm body 110, and the clamping arm 220 is preformed to be in contact with the clamping arm body 210, which is configured to ensure that the clamping arm 220 and the fixed arm 120 have a good return effect, and then ensure a clamping force between the clamping arm 220 and the fixed arm 120. Ni—Ti alloy is generally used to form a memory alloy.

Further, as a specific embodiment of the heart valve clamp of the present application, an external edge of the fixed arm 120 and the clamping arm 220 are configured to have a fillet or chamfer. Specifically, the external edge of the fixed arm 120, the clamping arm 220, and the pulling arm 240 may touch the heart. Chamfers arranged on sides of the fixed arm 120, the clamping arm 220 and the pulling arm 240, and fillets arranged at the corners of the fixed arm 120, the clamping arm 220 and the pulling arm 240 can make the external edge of the entire heart valve clamp smoother and effectively reduce the degree of trauma. Fillet or chamfer can be obtained by a polishing process during production.

Further, as a specific embodiment of the heart valve clamp of the present application, external sides of the delivery sheath 400, the fixed arm mechanism 100 and the clamping arm mechanism 200 are all covered with a fiber suture cloth (not shown). Specifically, portions of the heart valve clamp that may be in contact with the human body are covered with fiber suture cloth. The fiber suture cloth can be used for the endothelial tissue to climb and reduce damage to organs and tissues during the operation, meanwhile make the clamping of the valve tight.

As shown in FIGS. 10 to 14, the heart valve clamp of the present application is described in reference to the treatment of mitral valve regurgitation as an example for detailed description. A surgery is performed via a transcatheter way to deliver the delivery sheath 400 to the left atrium. Subsequent operations are based on this operation.

Firstly, the heart valve clamp is arranged in the left atrium through the delivery sheath 400, the heart valve clamp is delivered to a lower part of the valve, and the pulling arm base 230 is pushed through the push rod 300, and then the pulling arm 240 is opened to a certain angle through the clamping arm 220, the heart valve clamp is pulled up so that the clamping arm 220 cover the valve leaflet 600 from the bottom, and then the pulling wire 500 is released to open the fixed arm 120 and firmly press the valve leaflet 600 onto the clamping arm 220. After determining a proper clamping position of the valve leaflet 600 and achieving the regurgitation treatment effect, the push rod 300 is retracted for a certain distance to complete the closing step of the heart valve clamp, and a clamping effect can be determined again. If the regurgitation is reduced to an acceptable level, the push rod 300 can be withdrawn to a proximal end of the sheath hanger 140 to complete the release step of the heart valve clamp. The above steps can be repeated if necessary, until a desired effect is reached.

The pulling wire 500 of the clamp is respectively connected to two fixed arms 120, and an open angle of single fixed arm 120 can be independently controlled by adjustment. When the push rod 300 has not retracted to the position of the sheath hanger 140, the heart valve clamp can be opened to release the fixed valve leaflet 600, and the above implantation steps can be repeated to achieve a fully recoverable operation, which can greatly reduce a risk for implantation.

Certainly, the above-mentioned embodiments are only examples for clear description, and are not intended to restrict the embodiment. For an ordinary person skilled in the art, other changes or modifications in different forms can be made on the basis of the above description. It is unnecessary and impossible to list all the embodiments herein. The obvious changes or modifications derive therefrom still fall within the protection scope of the present application.

What is claimed is:

1. A heart valve clamp, comprising
   a fixed arm mechanism, comprising a fixed arm body and at least two fixed arms, extending outward from the fixed arm body, and integrally formed with the fixed arm body;
   a clamping arm mechanism, comprising a clamping arm body connected to a bottom of the fixed arm body to allow the clamping arm mechanism and the fixed arm mechanism to be fixedly connected to each other for clamping the leaflets of a heart valve, at least two clamping arms, extending outward from the clamping arm body, and integrally formed with the clamping arm body, a pulling arm base, and at least two pulling arms extending outward from the pulling arm base, wherein the pulling arm base is located at a bottom of the clamping arm body, and the at least two pulling arms are integrally formed with the at least two clamping arms;
   a driving mechanism, comprising a first driving assembly that drives the fixed arm to open or close in relation to the fixed arm body, and a second driving assembly that drives the clamping arm to open or close in relation to the clamping arm body, and
   a delivery sheath fixed on a top of the fixed arm body, wherein
   the fixed arm mechanism further comprises a sheath hanger on the top of the fixed arm body, and the sheath hanger is detachably and fixedly connected with the delivery sheath,
   the sheath hanger has at least one T-shaped hook protruding from the top of the fixed arm body and a fixing groove is arranged at a bottom of the delivery sheath for receiving the sheath hanger, and the fixing groove is engaged with the sheath hanger, is bendable, and is separable from the engagement, and
   the fixed arm mechanism and the clamping arm mechanism are both made of shape memory alloy.

2. The heart valve clamp according to claim 1, wherein the fixed arm body has a tube structure, and
   a side wall of the tube structure is provided with a first strip groove, and a tube wall disposed in the first strip groove is the fixed arm.

3. The heart valve clamp according to claim 1, wherein the fixed arm is preformed to open in a direction away from the fixed arm body, and
   the first driving assembly comprises at least two pulling wires, and an end of each pulling wire is respectively fixedly connected to a fixed arm and drives a single fixed arm or a plurality of fixed arms to open or close.

4. The heart valve clamp according to claim 3, wherein a fixing hole is arranged at an end of the fixed arm away from the fixed arm body for fixing the pulling wire.

5. The heart valve clamp according to claim 1, wherein a barbed structure is arranged on one side of the fixed arm facing the clamping arm.

6. The heart valve clamp according to claim 1, wherein
   a connection point between the pulling arm and the clamping arm is spaced apart from the clamping arm body.

7. The heart valve clamp according to claim 6, wherein the pulling arm base is a tube structure, and
   a side wall of the tube structure is provided with a second strip groove, a tube wall disposed in the second strip groove is regarded as the pulling arm, and a tube wall disposed outside the second strip groove is provided with a third strip groove, and an inner tube wall of the third strip groove forms the clamping arm and the clamping arm body.

8. The heart valve clamp according to claim 6, wherein the second driving assembly comprises a push rod slidably disposed through the fixed arm body and the clamping arm body and abutting against the pulling arm base.

9. The heart valve clamp according to claim 8, wherein the clamping arm is preformed to fit on the clamping arm body, and
   the push rod can drive the pulling arm base to move toward a side away from the clamping arm body, and drive the clamping arm to open.

10. The heart valve clamp according to claim 1, wherein there are two fixed arms and two clamping arms, the two fixed arms are symmetrical,
    the two clamping arms are symmetrical, and
    the fixed arms are arranged directly opposite to the clamping arms.

11. The heart valve clamp according to claim 1, wherein a maximum opening angle of the fixed arm is greater than or equal to a maximum opening angle of the clamping arm.

12. The heart valve clamp according to claim 1, wherein each of an external edge of the fixed arm and the clamping arm is configured to have a fillet or chamfer.

13. The heart valve clamp according to claim 1, wherein each of an external side of the fixed arm mechanism and the clamping arm mechanism is covered with fiber suture cloth.

14. The heart valve clamp according to claim 1, wherein
    the fixed arm is preformed to open in a direction away from the fixed arm body, and the first driving assembly comprises at least two pulling wires, and
    an end of each pulling wire is respectively fixedly connected to a fixed arm and drives a single fixed arm or a plurality of fixed arms to open or close.

15. The heart valve clamp according to claim 1, wherein a barbed structure is arranged on one side of the fixed arm facing the clamping arm.

* * * * *